(12) United States Patent
Deshpande et al.

(10) Patent No.: US 6,555,679 B2
(45) Date of Patent: Apr. 29, 2003

(54) METHOD FOR PREPARATION OF CEFTIOFUR SODIUM FROM ITS HYDROHALIDE SALTS

(75) Inventors: Pandurang Balwant Deshpande, Chennai (IN); Bhausaheb Pandarinath Khadangale, Chennai (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 0 days.

(21) Appl. No.: 09/968,854

(22) Filed: Oct. 3, 2001

(65) Prior Publication Data

US 2003/0065168 A1 Apr. 3, 2003

(51) Int. Cl.[7] ............................................. C07D 501/36
(52) U.S. Cl. ...................................... 540/226; 540/227
(58) Field of Search ................................. 540/226, 227

(56) References Cited

U.S. PATENT DOCUMENTS

| 4,464,367 A |   | 8/1984 | Labeeuw et al. |
| 4,877,782 A |   | 10/1989 | Cazers et al. |
| 4,902,683 A |   | 2/1990 | Amin et al. |
| 4,937,330 A | * | 6/1990 | Sacks et al. ................. 540/227 |

FOREIGN PATENT DOCUMENTS

| EP | 0 233 255 B1 | * | 8/1987 |
| WO | WO 02/42266 A2 |   | 5/2002 |

* cited by examiner

Primary Examiner—Mukund Shah
Assistant Examiner—Kahsay Habte
(74) Attorney, Agent, or Firm—Burns, Doane, Swecker & Mathis, L.L.P.

(57) ABSTRACT

The present invention relates to a process for preparing sodium salt of cephalosporins from their corresponding hydrohalide salt, which is neutralized with trimethylsilylating agent for the first time.

9 Claims, No Drawings

METHOD FOR PREPARATION OF CEFTIOFUR SODIUM FROM ITS HYDROHALIDE SALTS

FIELD OF THE INVENTION

The present invention discloses a new and economical process for preparation of ceftiofur acid starting from ceftiofur acid hydrohalide salt and treating it with a trimethylsilylating agent. The ceftiofur acid thus prepared was converted into its sodium slat by using some highly efficient sodium exchange reagent.

BACKGROUND OF THE INVENTION

Ceftiofur acid is the generic name given to a compound of formula (I)

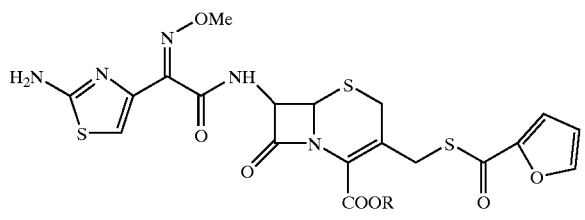

ceftiofur acid, its salts with alkali metal, alkaline earth metal and amines are reported for the first time in U.S. Pat. No. 4,464,367. All these derivatives of ceftiofur acid are known to have stability problems and are difficult to purify due to the amorphous nature of the compounds.

An attempt to overcome these problems was made in U.S. Pat. No. 4,877,782 by preparing zinc complexes of ceftiofur acid which have better dispersibility in water and can be used in pharmacological preparations. U.S. Pat. No. 4,902,683, explains the isolation of ceftiofur acid in the form of crystalline hydrohalide salts which has better solubility and other physical properties compared to parent compounds. The hydrohalide salts as such cannot be used for parenteral administration, therefore it is necessary to convert to a hydrohalide salt to sodium salt in order to use the drug as injectable.

Several methods are reported in patents for converting cephalosporanic acid to their corresponding alkali metal salt. This step is of special importance in the case of injectable antibiotics. Surprisingly, very few methods are disclosed for preparing ceftiofur sodium starting from hydrohalide salt of ceftiofur acid. U.S. Pat. No. 4,937,330 describes the use of polyvinylpyridine for neutralization of hydrohalide salt to get free acid and then treating the free acid with sodium-2-ethylhexanoate. The use of sodium-2-ethyl hexanoate for this purpose is the subject of several patents in the field of ceftiofur sodium antibiotics. The neutralization of hydrohalide salt using polyvinyl pyridine resin involves an extra filtration step in the process and the resin loses activity after certain batches and needs replacement which adds cost to the process.

In general, the process for liberation of ceftiofur acid free acid from hydrohalide salt using either resinous bases or non-resinous bases is associated with several problems. Keeping all these problems in mind, the Applicant discloses a simple, economical and commercially viable process for preparing ceftiofur sodium starting from ceftiofur acid hydrohalide salt which obviates the above mentioned limitations and does not use known neutralizing agents for this purpose. The process comprises two steps:

(a) treatment of hydrohalide salt of ceftiofur acid with trimethylsilylating agent which will neutralize the ceftiofur acid hydrohalide salt to give free ceftiofur acid; and (b) the reaction of free ceftiofur acid with sodium exchanging agents for making sodium salt of ceftiofur acid.

OBJECTS OF THE INVENTION

The primary object of the invention is a new process for preparing a ceftiofur sodium.

Another object of this invention is to neutralize the hydrohalide salt of ceftiofur acid to get free ceftiofur acid. This has been achieved by using N,O-bistrimethylsilyl acetamide, bis-trimethylsilylurea and Hexamethyl disilazane (HMDS). The applicant reports for the first time the use of these trimethylating agents for the purpose of neutralizing the hydrohalide salt of any cephem acid.

Yet another object of the invention relates to use of trimethylsilylating agent for the first time for the purpose of neutralizing the hydrohalide salt of any cephem acid.

Still another object of this invention is to make sodium salt thus prepared from ceftiofur acid using sodium lactate, sodium ethylacetoacetate, sodium-2-ethyl hexanoate and sodium acetate as sodium exchange reagent.

SUMMARY OF THE INVENTION

The present invention relates to a process for preparing sodium salt of cephalosporins from their corresponding hydrohalide salt, which is neutralized with trimethylsilylating agent for the first time.

DETAILED DESCRIPTION OF THE INVENTION

According to this invention treatment of hydrohalide salt of ceftiofur acid with a silylating agent in an aprotic solvent at a temperature ranging from 25 to 60° C. for 8–12 hrs gives free acid. The hydrohalide salt of ceftiofur acid employed in the present invention is well-known and commercially available. Hence, the present invention relates to a process for preparing ceftiofur sodium of formula (II)

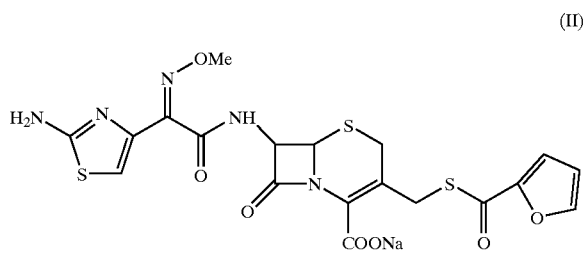

the said process comprising:

(a) dissolving and neutralizing the hydrohalide salt of ceftiofur acid using a silylating agent in an aprotic organic solvent and precipitation of a ceftiofur acid by quenching in water, and (b) dissolving the ceftiofur acid of step (a) in a solvent and reacted with a sodium exchanging reagent dissolved in a suitable solvent and precipitating ceftiofur sodium with ethylacetate or acetone.

Since the solubility of hydrohalide salt of ceftiofur acid is very poor in organic solvent and in aqueous phase, it is required to be solublize before neutralization takes place.

Silylating agents such as N,O-bistrimethylsilyl acetamide, bis silyl-urea (BSU) and hexamethyl disilazane (HMDS) used herein plays a dual role in this reaction. First, it solubilizes the hydrohalide salt of ceftiofur acid in an aprotic organic solvent and the by-product of this reaction neutralizes the hydrohalide salt, thus avoiding use of any other base. The silylating agent was used in mole ration of 1.0 to 5.0 w.r.t. hydrohalide salt but the most preferred ratio is about 3.0 moles w.r.t. hydrohalide salt of ceftiofur acid.

The solvents used in the process are selected from any of tetrahydrofuran, dixoane, Dichloromethane, dimethylacetamide (DMAc), acetone, acetonitrile and mixtures thereof. Most suitable solvents were acetonitrile and DMAc. The reaction was carried out at temperature range of 25–60° C. but best results were obtained at 35–40° C. The reaction duration was about 8–12 hours.

The wet cake of ceftiofur acid thus obtained was converted to sodium salt using sodium exchanging agents like sodium lactate, sodium ethyl acetoacetate, sodium acetate and sodium 2-ethyl hexanoate. Ceftiofur acid was dissolved in suitable solvent and reacted with suitable sodium-exchanging reagent, whereby the ceftiofur sodium product was precipitated by the addition of ethyl acetate or acetone.

The preferred process of this invention is to prepare sodium salt of ceftiofur acid starting from hydrohalide salt of ceftiofur acid.

The invention is illustrated with following examples but it should be understood that the invention is not intended to be limited to the specific embodiments herein.

EXAMPLE 1

7-[2-(2-amino-1,3-thiazol-4-yl)-(2-methyoxyimino) acetamido]-3-[(fur-2-ylcarbonyl)thiomethyl]-3-cephem-4-carboxylic acid A sample of ceftiofur acid hydrochloride salt (25.0) was suspended in acetonitrile (125 ml) around 28–30° C. N,O bis trimethylsilyl acetamide (27.5 gm) was added slowly. The temperature rose up to 45° C. The resultant solution was stirred for 8–9 hours at 28–30° C. The solution was added to water (1000 ml) and stirred at 28–30° C. for 45–50 minutes. The solid material obtained was filtered and washed with water (2×50 ml). Product was dried under vacuum at 40–42° C. for 6–8 hours to give 20g title compound.

EXAMPLE-2

7-[2-(2-amino-1,3-thiazol-4-yl)-(2-methoxyimino) acetamido]-3-[(fur-2-ylcarbonyl)thiomethyl]-3-cephem-4-carboxylic acid A sample of ceftiofur acid hydrochloride salt (25.0 g) was suspended in dimethylacetamide (150 ml) around 28–30° C. N,O bis trimethylsilyl acetamide (27.5 gm) was added. The temperature rose upto 45° C. The resultant solution was stirred for 8–9 hours at 28–30° C. The solution was added to water (1000 ml) and stirred at 28–30°C. for 45–50 minutes. The solid material obtained was filtered and washed with water (2×50 ml). Product was dried under vacuum at 40–42° C. for 6–8 hours to give (19g) title compound.

EXAMPLE-3

7-[2-(2-amino-1,3-thiazol-4-yl)-(2-methoxyimino) acetamide]-3-[(fur-2-ylcarbonyl)thiomethyl]-3-cephem-4-carboxylic acid A sample of ceftiofur acid hydrochloride salt (25.0 g) was suspended in acetonitrile (125 ml) around 28–30° C. Bissilylurea (BSU) (35 gm) was added slowly to it. The temperature rose upto 45° C. The resultant solution was stirred for 8–9 hours at 28–30° C. The solution was added to water (1000 ml) and stirred at 28–30° C. for 45–50 minutes. The solid material obtained was filtered and washed with water (2×50 ml). Product was dried under vacuum at 40–42° C. for 6–8 hours to give (20g) title compound.

EXAMPLE-4

7-[2-(2-amino-1,3-thiazol-4-yl)-(2-methoxyimino) acetamido]-3-[(fur-2-ylcarbonyl)thiomethyl]-3-cephem-4-carboxylic acid A sample of ceftiofur acid hydrochloride salt (25.0 g) was suspended in acetonitrile (125 ml) around 28–30° C. Hexamethyl disilazane (40 gm) was added slowly. The temperature rose upto 45° C. The resultant solution was stirred for 8–9 hours at 28–30° C. The solution was added to water (1000 ml) and stirred at 28–30 C. for 45–50 minutes. The solid material obtained was filtered and washed with water (2×50 ml). Product was dried under vacuum at 40–42° C. for 6–8 hours to give (20g) title compounds.

EXAMPLE-5

Sodium 7-[2-(2-amino-1,3-thiazol-4-yl)-(2-methoxyimino)acetamido]-3-[(fur-2-ylcarbonyl) thiomethyl]-3-cephem-4-carboxylate A sample of ceftiofur acid (5.0 gm, anhydrous basis) was suspended in methanol (25 ml) around 20–22° C. Triethylamine (1 g) was added dropwise in 20 minutes. The solution was treated with carbon and filtered off at 20–25° C. A solution of sodium lactate 60% w/w (1.7 g) in methanol (10 ml) at 28° C., was added drop wise and stirred. Acetone (165 ml) was added further for complete crystallization at 20–25° C. The crystalline product formed was filtered and washed with ethyl acetate (3×10 ml), product was dried under vacuum at 40–42° C. for 3–4 hours to get 3.8 gm of ceftiofur sodium (purity by HPLC 97.0%)

EXAMPLE-6

Sodium 7-[2-(2-amino-1,3-thiazol-4-yl)-(2-methoxyimino)acetamido]-3-[(fur-2-ylcarbonyl) thiomethyl]-3-cephem-4-carboxylate acid A sample of ceftiofur acid (5.0 g, anhydrous basis) was suspended in methanol (25 ml) around 20–22° C. Triethylamine (1.0 gm) was added dropwise in 20 minutes. The resultant solution was treated with carbon and filtered off at 20–25° C. A solution of ethyl acetoacetate sodium salt (1.5 g) in 10 ml of methanol was added dropwise to ceftiofur acid solution around 20–25° C. and stirred. Ethyl acetate (40 ml) was added further for complete crystallization at 20–28° C. The crystals were filtered and washed with ethyl acetate (3×10 ml). Product was dried under vacuum at 40–42° C. for 3–4 hours to get 3.73 gm of ceftiofur sodium (purity by HPLC 98.0%).

EXAMPLE 7

Wet ceftiofur acid (2.5 gm on anhydrous basis, 4.7 mmol) was dissolved in tetrahydrofuran (45 ml) and the resultant clear solution was treated with sodium-2-ethyl hexanoate (1.2 gm, 7.2 mmol) at room temperature for 10 minutes. Acetone was added to precipitate out of the ceftiofur sodium in crystalline form, which was separated by filtration. Solid was washed with acetone and dried at 40–42° C. to get 1.8 gm of ceftiofur sodium (purity by HPLC>97%).

EXAMPLE 8

Wet ceftiofur acid (2.5 gm on anhydrous basis, 4.7 mmol) was dissolved in tetrahydrofuran (45 ml) and the resultant clear solution was treated with sodium ethylacetoacetate (1.1 gm, 7.3 mmol) at room temperature for 10 minutes. Acetone was added to precipitate out the sodium ceftiofur in crystalline form, which was separated by filtration. Solid was washed with acetone and dried at 40–42° C. to get 1.9 gm of ceftiofur sodium (purity by HPLC>98%).

EXAMPLE 9

A sample of ceftiofur acid (5.0 g, anhydrous basis) was suspended in methanol (25 ml) around 20–22° C. Triethylamine (1.0 gm) was added dropwise in 20 minutes. The resultant solution was treated with carbon and filtered off at 20–25° C. A solution of anhydrous sodium acetate (1.5 g) in 20 ml of methanol was added dropwise to ceftiofur acid solution around 20–25° C. Ethylacetate (40 ml) was added further for complete crystallization around 20–28° C. The crystals were filtered and washed with ethyl acetate (3×10 ml). Product was dried under vacuum at 40–42° C. for 3–4 hours to get 3.73 gm of ceftiofur sodium (purity by HPLC 97.0%).

We claim:

1. A process for preparing a ceftiofur sodium of formula (II)

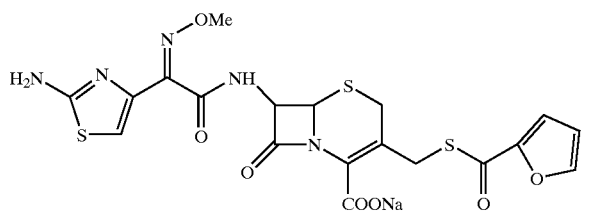

said process comprising:
(a) dissolving and neutralizing the hydrohalide salt of ceftiofur acid using a silylating agent in an aprotic organic solvent and precipitation of a ceftiofur acid, and
(b) dissolving the ceftiofur acid from step (a) in a solvent and reacting same with a sodium exchanging reagent dissolved in a suitable solvent and precipitating ceftiofur sodium therefrom.

2. The process of claim 1, wherein the silylating agents are selected from N,O - bis trimethylsilyl acetamide, hexamethyldisilazane (HMDS), bissilylurea (BSU) and mixtures thereof, preferably N,O - bistrimethylsilyl acetamide.

3. The process of claim 1, wherein in step (a) the aprotic organic solvent is selected from the group comprising acetone, tetrahydrofuran, acetonitrile, dioxane, dimethylacetamide and mixtures thereof.

4. The process of claim 1, wherein the sodium exchanging reagent in step (b) is selected from sodium lactate, sodium ethyl acetoacetate, sodium acetate and sodium-2-ethyl hexanoate.

5. The process of claim 1, wherein in step (b) the precipitation of ceftiofur sodium is effected using ethylacetate or acetone.

6. The process of claim 2, wherein the amount of silylating agent used is in the ratio of 1.0 moles to 5.0 moles with respect to hydrohalide salt of ceftiofur acid, preferably 3 moles.

7. The process of claim 1, wherein in step (a) the hydrohalide salt is selected from hydrochloride and hydrobromide.

8. The process of claim 1, wherein in steps (a) and (b) the reaction is effected at a temperature range of 25° to 60° C., preferably at 45° C.

9. The process of claim 1, wherein in step (b) the solvent used is selected from a group comprising tetrahydrofuran and methanol.

* * * * *